(12) United States Patent
Brugnoli

(10) Patent No.: US 9,581,539 B2
(45) Date of Patent: Feb. 28, 2017

(54) DEVICE FOR MEASURING THE CONSUMPTION OF OXYGEN AND THE CONSUMPTION OF CARBON DIOXIDE BY A SUBJECT

(71) Applicant: COSMED S.r.l., Rome (IT)

(72) Inventor: Paolo Brugnoli, Albano Laziale (IT)

(73) Assignee: COSMED S.r.l., Rome (IT)

( * ) Notice: Subject to any disclaimer, the term of this patent is extended or adjusted under 35 U.S.C. 154(b) by 355 days.

(21) Appl. No.: 14/162,219

(22) Filed: Jan. 23, 2014

(65) Prior Publication Data

US 2014/0235961 A1 Aug. 21, 2014

(30) Foreign Application Priority Data

Feb. 21, 2013 (EP) .................................. 13156169

(51) Int. Cl.
*A61B 5/087* (2006.01)
*G01N 19/10* (2006.01)
(Continued)

(52) U.S. Cl.
CPC ............. *G01N 19/10* (2013.01); *A61B 5/087* (2013.01); *A61B 5/0833* (2013.01); *A61B 5/0836* (2013.01); *A61B 5/097* (2013.01)

(58) Field of Classification Search
None
See application file for complete search history.

(56) References Cited

U.S. PATENT DOCUMENTS 4,509,359 A 4/1985 Gedeon et al.
4,512,191 A * 4/1985 Sexton ..................... G12B 9/06
73/29.02

(Continued)

FOREIGN PATENT DOCUMENTS

DE 196 19 763 11/1997
DE 197 31 889 1/1999

OTHER PUBLICATIONS

Search Report for EP 13 15 6169 dated Aug. 14, 2013.

*Primary Examiner* — Kennedy Schaetzle
(74) *Attorney, Agent, or Firm* — Nixon & Vanderhye P.C.

(57) ABSTRACT

A device for measuring the consumption of oxygen and the consumption of carbon dioxide by a subject comprises an air collecting member for collecting the flow of air breathed, a flowmeter for measuring the flow rate of air exhaled by the subject, and a sampling line for sampling a portion of the flow of air exhaled by the subject. A pump, with substantially constant capacity draws the aforesaid portion of flow of air into the sampling line. A mixing chamber is interposed in the sampling line for collecting and mixing together flows of air exhaled by the subject in a number of breathing cycles. Means for sensing the concentration of oxygen and means for sensing the concentration of carbon dioxide are arranged in the sampling line. The pump is with constant capacity, but is controlled in a PWM mode in order to simulate a capacity that varies in proportion to the variation of the flow during the breathing cycle so as to render measurement of the consumption of oxygen reliable even though the mixing chamber does not receive the entire flow exhaled by the subject. The device further comprises a bypass line of the mixing chamber, through which the flow of air can pass without passing through the mixing chamber. A valve for selecting the measuring mode can be displaced selectively into two different positions, to get the flow of air that traverses the sampling line to converge either through the mixing chamber, when an average measurement is to be made of the consumption of oxygen by the subject in the course of a number of breathing cycles, or through said bypass line, when an instantaneous measurement is to be made of the consumption of oxygen by the subject in each breathing cycle.

2 Claims, 4 Drawing Sheets

(51) Int. Cl.
*A61B 5/097* (2006.01)
*A61B 5/083* (2006.01)

(56) References Cited

U.S. PATENT DOCUMENTS

| | | | |
|---|---|---|---|
| 4,631,966 A | 12/1986 | Brugnoli | |
| 4,658,832 A | 4/1987 | Brugnoli | |
| 6,039,696 A * | 3/2000 | Bell | A61M 16/08 128/204.21 |
| 6,206,837 B1 | 3/2001 | Brugnoli | |
| 6,724,612 B2 * | 4/2004 | Davis | G01N 27/225 361/280 |
| 2006/0005836 A1 | 1/2006 | Brugnoli | |
| 2006/0020221 A1 * | 1/2006 | Silpachai | A61B 5/097 600/538 |
| 2008/0125700 A1 * | 5/2008 | Moberg | A61M 5/14244 604/67 |

* cited by examiner

DEVICE FOR MEASURING THE CONSUMPTION OF OXYGEN AND THE CONSUMPTION OF CARBON DIOXIDE BY A SUBJECT

FIELD OF THE INVENTION

The present invention relates to devices for measuring the consumption of oxygen and the consumption of carbon dioxide by a subject. In particular the invention regards a device of the type comprising:

- an air collecting member for collecting a flow of air, such as a face mask or a mouthpiece, which can be worn by the subject and has passages for the air inhaled and exhaled by the subject;
- a flowmeter that can be associated to the collecting member, for measuring the flow rate of air exhaled by the subject;
- a sampling line connected to the collecting member or to the flowmeter, for sampling a portion of the flow of air exhaled by the subject;
- a suction pump, with substantially constant capacity, arranged downstream of the sampling line, for drawing the aforesaid portion of flow of air into the sampling line;
- a mixing chamber interposed in the sampling line, upstream of the suction pump, for collecting and mixing together flows of air exhaled by the subject in a number of breathing cycles;
- means for sensing the concentration of oxygen, and means for sensing the concentration of carbon dioxide, arranged in the sampling line between the mixing chamber and the suction pump, for measuring the concentration of oxygen and of carbon dioxide in the flow of air that traverses the sampling line downstream of the mixing chamber;
- a switching valve for switching the intake of the pump between a condition of connection to the sampling line and a condition in which said connection is interrupted and the intake of the pump communicates with a line for intake of air from the environment; and
- an electronic control unit for receiving and processing the signals emitted by said flowmeter, by said means for sensing the concentration of oxygen and by said means for sensing the concentration of carbon dioxide in order to obtain an average measurement of the consumption of oxygen and the consumption of carbon dioxide by the subject in the course of a number of breathing cycles, said electronic control unit being moreover provided for controlling said switching valve in a PWM (Pulse Width Modulation) mode, in order to simulate a capacity of the suction pump that varies in proportion to the variation of the flow during the breathing cycle so as to render reliable the measurement of the consumption of oxygen and carbon dioxide, even though the mixing chamber does not receive the entire flow exhaled by the subject.

KNOWN ART

A device of the type referred to above has for some time been produced and marketed by the present applicant. Devices of the same type are also illustrated in the documents U.S. Pat. Nos. 4,631,966, 4,658,832 (filed in the name of the present applicant) and the document No. U.S. 2006/0005836 (filed in the name of a company connected to the present applicant).

Devices of the above type are characterized in that they enable average measurements of the consumption of oxygen and carbon dioxide by the subject within a number of breathing cycles, thanks to the use of the aforesaid mixing chamber. At the same time, said devices may even be produced with relatively small dimensions (so as to be portable), thanks to the fact that the mixing chamber must receive only a portion of the flow exhaled by the subject. This does not alter the reliability of the measurement in so far as, as has been mentioned above, there is simulated a capacity of the suction pump that varies in proportion to the variation of the flow during the breathing cycle.

Likewise known are devices that adopt the so-called technique of the "breath-by-breath" measurement, designed to carry out an instantaneous measurement of the consumption of oxygen and carbon dioxide during each breathing cycle of the subject. The above devices are basically constituted in a way similar to the devices with mixing chamber described above, except for the fact that no mixing chamber is inserted in the sampling line and for the fact that the suction pump activates a constant flow of uniform flow rate through the sampling line. Breath-by-breath measuring devices have also been produced and marketed for some time by the present applicant. A device of this type is moreover described and illustrated in the document U.S. Pat. No. 6,206,837, which is also filed in the name of the present applicant.

For applications in the clinical field, the devices of the breath-by-breath type are more indicated and preferred, whereas the devices with mixing chamber are better suited to measurements on athletes or subjects who in any case take part in sports.

OBJECTS OF THE INVENTION

The main object underlying the present invention is to provide a device that will be able to operate selectively in both of the modes described above, i.e., with average measurement by means of the mixing chamber or with instantaneous breath-by-breath measurement.

A further object of the present invention is to achieve the aforesaid goal with a simple and functional device, of small overall dimensions (and consequently suited to being produced also in a portable form), and reliable as regards its operation.

A secondary object is to guarantee the reliability of the measurement in any condition of operation and in particular even in the case of an undesirable variation of the humidity of the flow of air in the sampling line with respect to the humidity of the environment.

Yet a further object is to enable simple and rapid operations of calibration of the device.

SUMMARY OF THE INVENTION

With a view to achieving one or more of the aforesaid objects, the subject of the invention is a device having all the characteristics referred to at the start of the present description and moreover characterized in that said device further comprises:

- a bypass line parallel to the mixing chamber, through which the flow of air can pass without passing through the mixing chamber, said bypass line merging again into in the sampling line upstream of the aforesaid sensor means;

a valve for selecting a measuring mode, which can be displaced selectively into two different positions, to cause the flow of air that traverses the sampling line to converge either through the mixing chamber, when an average measurement is to be made of the consumption of oxygen by the subject in the course of a number of breathing cycles, or through said bypass line, when an instantaneous measurement is to be made of the consumption of oxygen by the subject in each breathing cycle, said pump being kept constantly connected to the sampling line when the aforesaid instantaneous measuring mode is selected.

Thanks to the aforesaid arrangements, the device according to the invention is consequently able to operate selectively in both of the measuring modes described above, i.e., both with average measurement by means of the mixing chamber and with instantaneous breath-by-breath measurement. In both modes, the reliability of the measurement is guaranteed. All the advantages of the known solutions described above, are thus maintained without the drawbacks thereof.

According to a further preferred characteristic, the device of the invention is of the type in which said sampling line includes a tube having a wall permeable to humidity to keep the humidity within the sampling line substantially equal to ambient humidity. The device is moreover characterized in that it comprises:

first humidity-sensing means for sensing the humidity of the flow of air within the sampling line; and second humidity-sensing means, adapted to detect the humidity of the ambient air, said electronic control unit being provided for comparing the values of humidity measured by said first and second humidity-sensing means and for activating an alarm signal when the difference between said values exceeds a pre-set threshold, indicating the need to replace said tube with permeable wall defining said sampling line.

In a preferred embodiment, the device of the invention further comprises a calibration valve, arranged in the sampling line and switchable between a first condition, of connection of the downstream stretch of the sampling line with the aforesaid air collecting member for collecting a flow of air, and a second condition of connection of the downstream stretch of the sampling line with a further line for sampling the ambient air. Interposed in the above further line for sampling the ambient air is a device for absorbing carbon dioxide, to completely remove the content of carbon dioxide in the flow of air that traverses the aforesaid line. The electronic control unit is provided for keeping the calibration valve in the aforesaid second condition when the calibration mode is to be activated.

BRIEF DESCRIPTION OF THE FIGURES

Further characteristics and advantages of the invention will emerge from the ensuing description with reference to the annexed drawings, which are provided purely by way of non-limiting example in which.

DETAILED DESCRIPTION OF THE INVENTION

Figure 1:
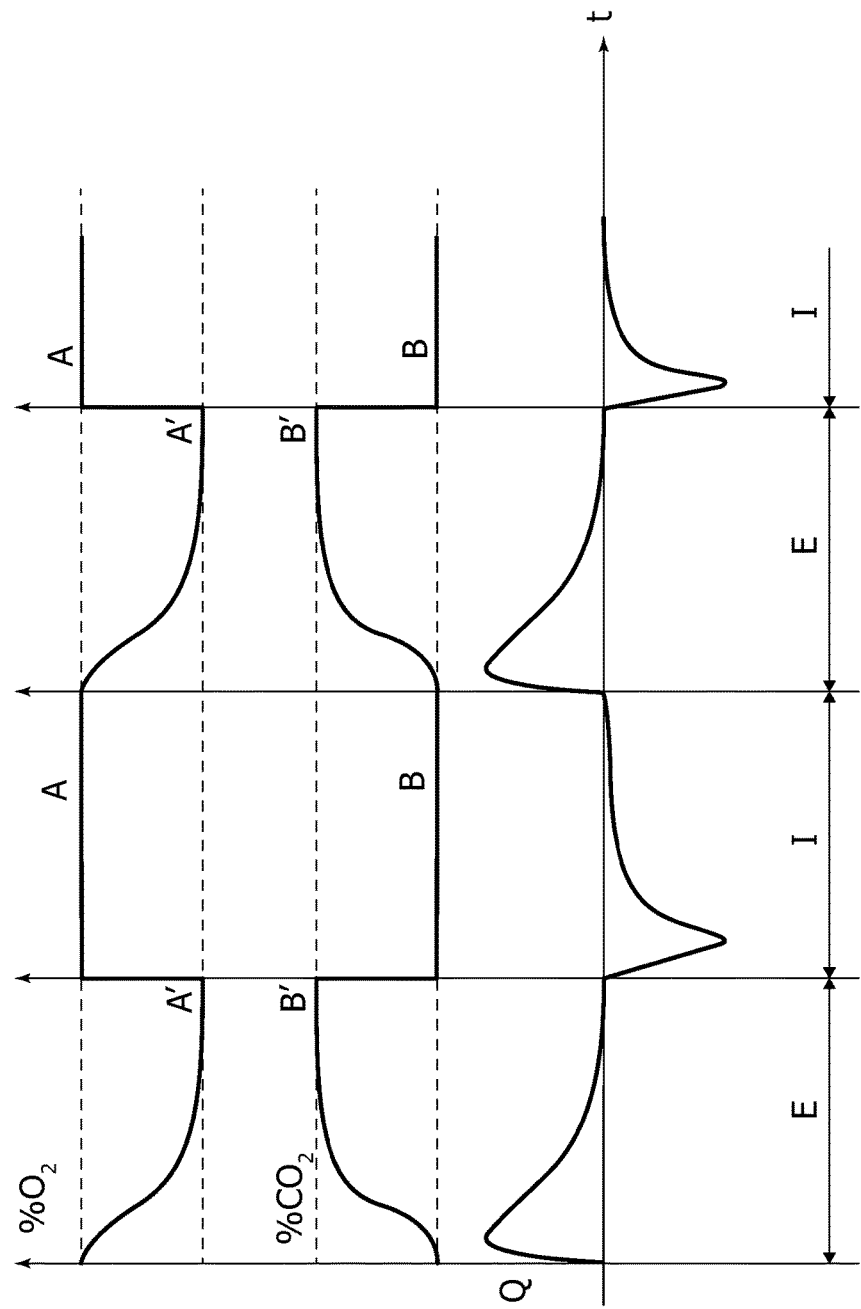
FIG. 1 illustrates plots that show the variation of the concentrations of oxygen and of carbon dioxide and the variation of the total flow of air during the steps of breathing in and of breathing out of a subject.

The breathing cycle comprises a step of breathing in—designated in FIG. 1 by the letter I—in which the ambient air is introduced into the lungs, and a step of breathing out—designated in FIG. 1 by the letter E—in which the air is expelled by the lungs into the environment.

The organism takes in oxygen during the step of breathing in I and eliminates carbon dioxide during the step of breathing out E.

FIG. 1 shows that during each step of breathing out E the flow of air exhaled has a concentration of oxygen that decreases progressively from an initial value A, which is approximately 20.93% (corresponding to the value of concentration of oxygen in the ambient air) down to a final value A' of approximately 16%.

Instead, the concentration of carbon dioxide during each step E undergoes a progressive increase from an initial value B of approximately 0.04% (corresponding to the concentration of carbon dioxide in the ambient air) up to a final value B' of approximately 5%.

The curve Q represents the total flow of air during each step of breathing out E and during each step of breathing in I.

The values of concentration of oxygen and of carbon dioxide of the inhaled air are practically constant and equal respectively to the aforesaid values A and B, in so far as they reflect the concentration of oxygen and of carbon dioxide in the ambient air.

The concentration of oxygen present in the exhaled air depends upon the amount of oxygen consumed by the subject, and the consumption of oxygen is directly proportional to the expenditure of energy.

The expenditure of energy in resting conditions is referred to as basal metabolism; the metabolic rates increase distinctly for example with physical exercise. A person who performs physical exercise consumes an amount of oxygen that is significantly higher than that consumed in resting conditions, and the consumption of oxygen increases in proportion with the expenditure of energy.

By measuring the consumption of oxygen, it is consequently possible to estimate the expenditure of energy of a subject; in particular, it has been proposed to adopt an empirical rule whereby to each litre of oxygen consumed there correspond approximately 5 kcal of energy produced by the organism.

As already illustrated above, the known art comprises both devices for carrying out measurement of the consumption of oxygen and carbon dioxide with instantaneous measurements of the breath-by-breath type and devices for average measurements on a number of breathing cycles, which envisage the use of a mixing chamber for the exhaled gases.

Figure 2:
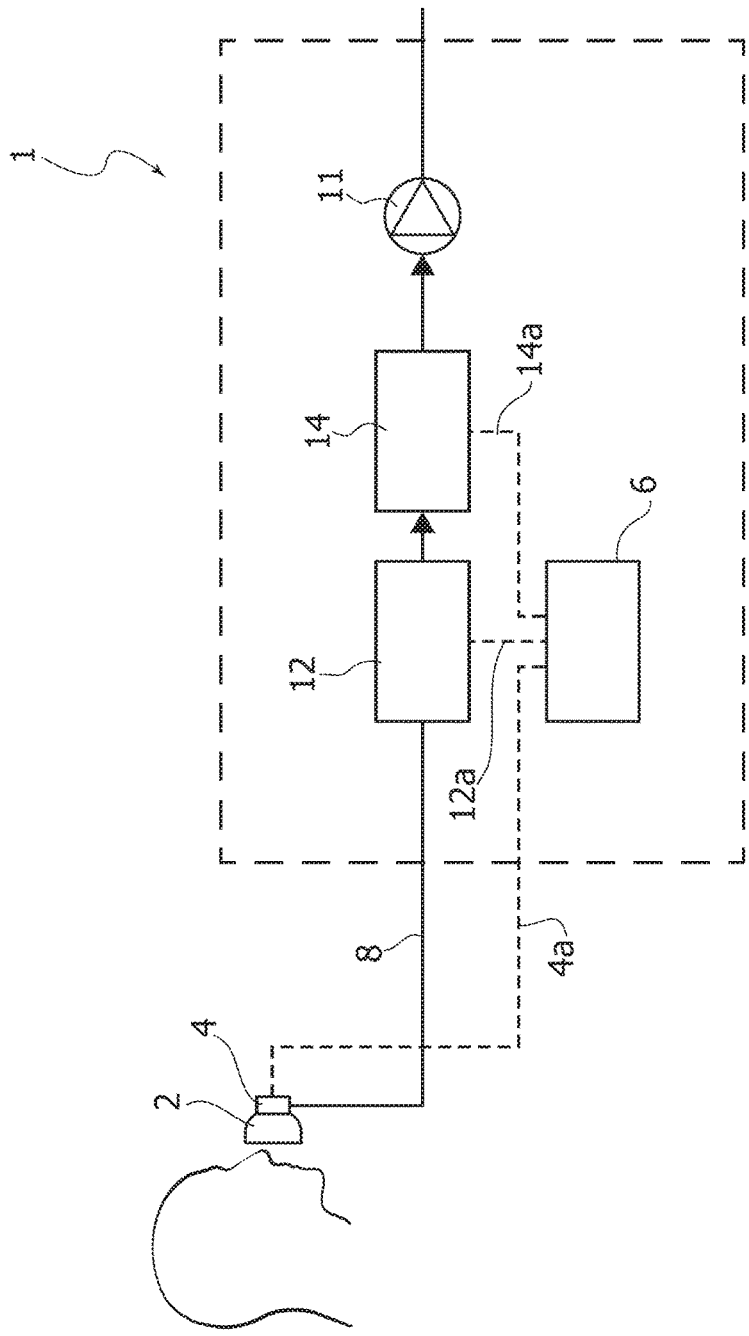
FIGS. 2 and 3 are diagrams that illustrate devices for measuring the concentrations of oxygen and carbon dioxide in the flow exhaled by a subject, obtained in accordance with the known art, and designed to carry out respectively measurements of the breath-by-breath type and measurements of the mixing-chamber type.

FIG. 2 is a diagram that illustrates a device of the breath-by-breath type according to the known art, designed to measure instantaneously the concentrations of oxygen and carbon dioxide in the flow of air exhaled by a subject in each breathing act.

The device, designated as a whole by the reference number 1, comprises an air collecting member 2 that has passages for enabling flow of the air inhaled and exhaled by the subject.

The air collecting member 2—for example a face mask or alternatively a mouthpiece—is worn by the subject at the moment of measurement. The constructional details of the aforesaid collecting member are not illustrated herein in so far as they can be obtained in any known way and do not fall, taken in themselves, within the framework of the invention. Moreover, their elimination from the drawings renders the latter of more readily and easily understandable.

A flowmeter 4 associated to the air collecting member 2 enables measurement of the flow rate of air exhaled by the subject.

A portion of the flow of air exhaled by the subject is taken from a sampling line 8 that is connected to the flowmeter 4.

In a different embodiment, the sampling line 8 can be connected to the collecting member 2.

The device 1 comprises a suction pump 11, with substantially constant capacity, arranged downstream of the sampling line 8 for drawing the aforesaid portion of flow of air into the above sampling line 8. Also for the pump 11, the constructional details are not illustrated herein in so far as it is of a known type.

In the sampling line 8, present between the flowmeter 4 and the suction pump 11 are means for sensing the concentration of oxygen 12 and means for sensing the concentration of carbon dioxide 14 that measure the concentration of oxygen and of carbon dioxide in the flow of air that traverses the sampling line 8.

Also the above sensor means may be provided in any known way and, for this reason, are not described in detail herein. In general, the aforesaid sensors exploit absorption of infrared radiation as regards carbon dioxide (infrared sensors) or the electrical charge produced by the chemical reaction of the oxygen with an electrolyte with which it is in contact (galvanic fuel cells).

The device 1 further comprises an electronic control unit 6 that receives and processes signals 4a emitted by the flowmeter 4, signals 12a emitted by the sensor means for detecting oxygen 12 and signals 14a emitted by the means for sensing the concentration of carbon dioxide 14, in order to obtain an instantaneous measurement of the consumption of oxygen and carbon dioxide in each breathing cycle.

The control unit 6 is programmed for calculating the values of the consumption of oxygen and carbon dioxide on the basis of the measurements made and according to predetermined computing algorithms.

Figure 3:
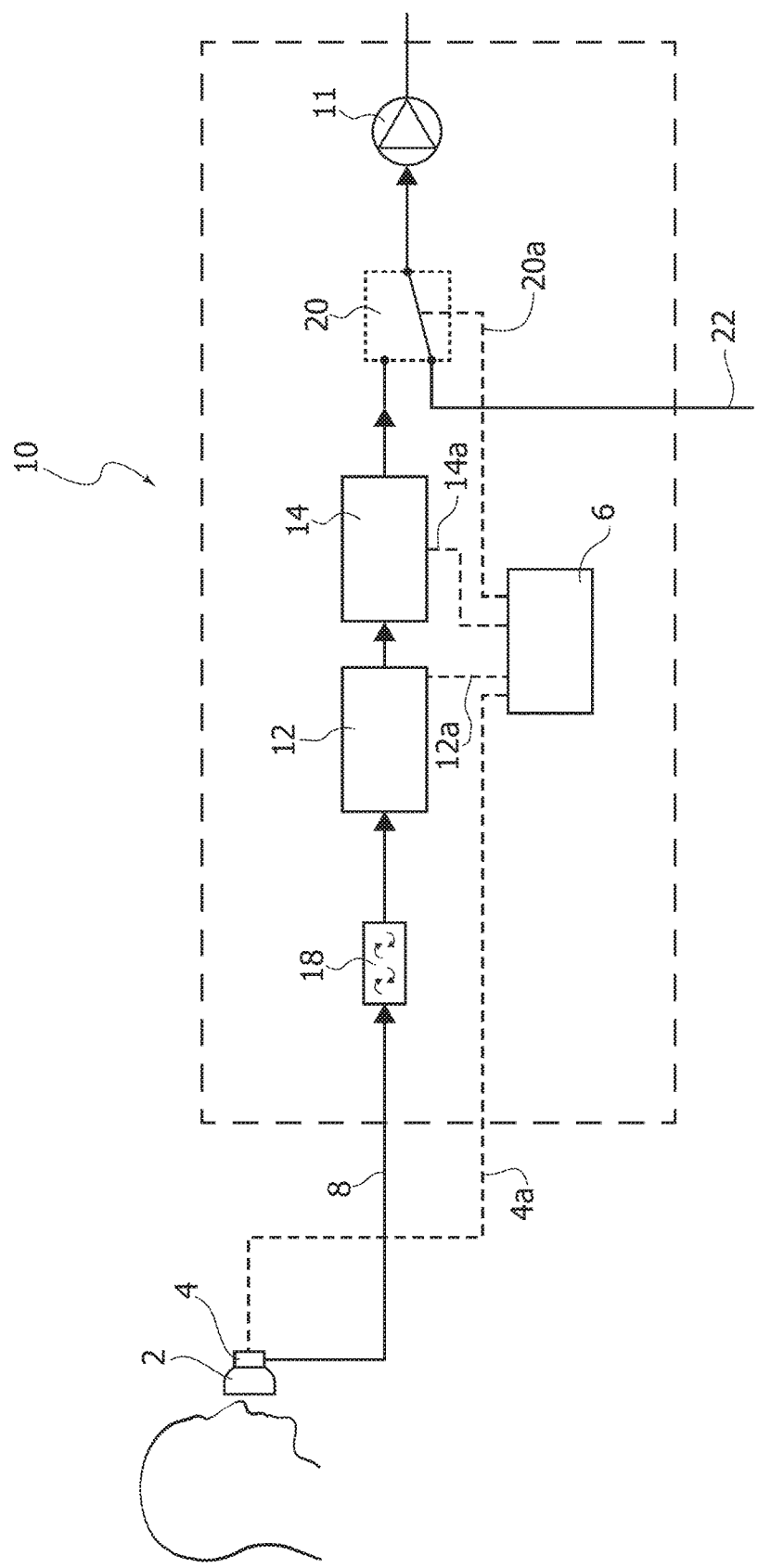

FIG. 3 is a diagram that illustrates a device according to the known art, of the type with mixing chamber, which enables detection of the average consumption of oxygen and carbon dioxide in a sample of air exhaled by a subject in a number of breathing cycles.

A device like the one represented in FIG. 3 has a mixing chamber of relatively small dimensions in so far as the aforesaid chamber is not designed to receive the entire flow exhaled by the subject, but only a portion of the aforesaid flow that is sampled in a sampling line.

In FIG. 3, the parts in common with FIG. 2 are designated by the same reference numbers. As may be seen, also in this case there are provided an air collecting member 2, a flowmeter 4 associated to the air collecting member 2 that enables measurement of the volume of air exhaled by the subject, and a suction pump 11, with substantially constant capacity, which draws in the exhaled air into the sampling line 8 connected to the flowmeter 4.

The device 10 represented in FIG. 3 further comprises a mixing chamber 18 interposed in the sampling line 8, upstream of the suction pump 11, for collecting and mixing together flows of air exhaled by the subject in a number of breathing cycles.

The device 10 comprises means for sensing the concentration of oxygen 12 and means for sensing the concentration of carbon dioxide 14 that are arranged in the sampling line 8 between the mixing chamber 18 and the suction pump 11 and that may be of the same type described with reference to FIG. 2. The aforesaid sensor means 12 and 14 measure the concentration of oxygen and of carbon dioxide in the flow of air that traverses the sampling line 8 downstream of the mixing chamber 18.

An electronic control unit 6 receives and processes signals 4a emitted by the flowmeter 4 and signals 12a, 14a emitted by the means for sensing the concentration of oxygen 12 and of carbon dioxide 14 in order to obtain an average measurement of the consumption of oxygen by the subject in the course of a number of breathing cycles.

The device 10 further comprises a switching valve 20 for switching the intake of the pump 11 between a condition of connection to the sampling line 8 and a condition in which the aforesaid connection is interrupted.

When the aforesaid connection is interrupted, the intake of the pump 11 communicates with a line 22 for intake of the ambient air.

The electronic control unit 6 is provided for controlling (line 20a) the switching valve 20 by actuator means of any a known type (not illustrated) in a PWM mode in order to simulate a capacity of the suction pump 11 that is variable and proportional to the variation of the flow during the breathing cycle (plot Q in FIG. 1) so as to render measurement of the consumption of oxygen reliable even though the mixing chamber 18 does not receive the entire flow exhaled by the subject.

The PWM control of the pump at constant capacity simulates a variation of the capacity corresponding to that of the flow Q exhaled by the subject under examination.

Thanks to the fact that the mixing chamber can, in this way, receive only a portion of the flow exhaled by the subject without altering the reliability of the measurement, the aforesaid devices may be produced with relatively small dimensions and may hence be portable.

As has been mentioned above, the known devices of the type illustrated in FIG. 2 and of the type illustrated in FIG. 3 each present advantages and drawbacks that render them suited to being used in different applications (for example, the former for clinical tests and the latter for tests on athletes).

Figure 4:
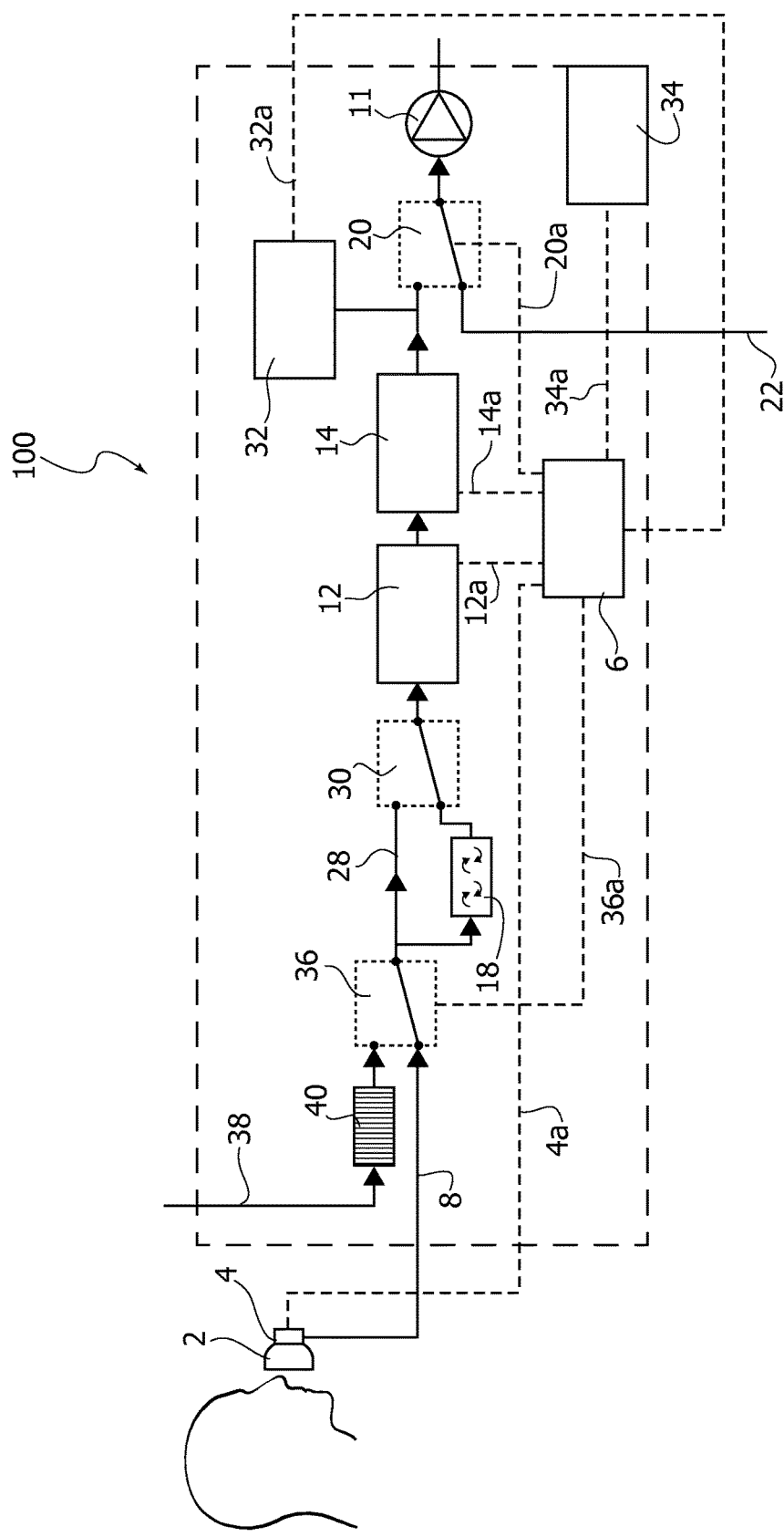
FIG. 4 is a diagram of a preferred embodiment of the device according to the invention.

FIG. 4 represents a diagram of a preferred embodiment of the device according to the invention that is able to operate selectively in both of the modes described above, i.e., with average measurement by means of the mixing chamber or with instantaneous breath-by-breath measurement.

The device 100 according to the invention presents all the characteristics that have been illustrated for the devices represented schematically in FIG. 2 and in FIG. 3, and the components identical to the ones described previously are designated by the same reference numbers.

The device 100 has an air collecting member 2 for collecting a flow of air, such as for example a face mask or a mouthpiece, which can be worn by the subject and has passages for the air inhaled and exhaled by the subject.

A flowmeter 4 designed to measure the flow rate of air exhaled by the subject may be associated to the air collecting member 2.

The device 100 has a sampling line 8 connected to the flowmeter 4. In a different embodiment, the sampling line 8 may be connected to the air collecting member 2.

The sampling line 8 samples a portion of the flow of air exhaled by the subject, and the aforesaid portion of the flow of air is sampled by a suction pump 11, with substantially constant capacity, arranged downstream of the sampling line 8.

The device 100 has a mixing chamber 18 interposed in the sampling line 8, upstream of the suction pump 11, for collecting and mixing together flows of air exhaled by the subject in a number of breathing cycles.

Means for sensing the concentration of oxygen 12 and means for sensing the concentration of carbon dioxide 14 are arranged in the sampling line 8 between the mixing chamber 18 and the suction pump 11 for measuring the concentration of oxygen and of carbon dioxide in the flow of air that traverses the sampling line 8 downstream of the mixing chamber 18.

The device 100 comprises a switching valve 20 for switching the intake of the pump 11 between a condition of connection to the sampling line 8 and a condition in which the aforesaid connection is interrupted and the intake of the pump communicates with a line 22 for intake of air from the environment.

The device 100 has an electronic control unit 6 for receiving and processing signals 4a emitted by the aforesaid flowmeter 4, signals 12a, 14a emitted by the aforesaid means for sensing the concentration of oxygen 12 and by the aforesaid means for sensing the concentration of carbon dioxide 14 in order to obtain an average measurement of the consumption of oxygen by the subject in the course of a number of breathing cycles.

The electronic control unit 6 is moreover prearranged for controlling (line 20a) the switching valve 20 in a PWM mode in order to simulate a capacity of the suction pump that varies in proportion to the variation of the flow during the breathing cycle so as to render measurement of the consumption of oxygen reliable, even though the mixing chamber does not receive the entire flow exhaled by the subject.

All the aforesaid components can be provided in a way similar to what is envisaged for the known devices of FIGS. 2 and 3.

The device 100 forming the subject of the present invention further comprises a bypass line 28 parallel to the mixing chamber 18, through which the flow of air can pass without passing through the mixing chamber 18. A valve 30 for selecting a measuring mode is interposed in the line downstream of the mixing chamber 18, downstream of the bypass line 28, and upstream of the sensor means 12 and 14. The aforesaid selection valve 30 can be displaced selectively into two different positions, designed to cause the flow of air that traverses the sampling line 8 to converge either through the mixing chamber 18, when an average measurement is to be made of the consumption of oxygen by the subject in the course of a number of breathing cycles, or else through the aforesaid bypass line 28, when an instantaneous measurement is to be made of the consumption of oxygen by the subject in each breathing cycle. In the latter case, the flow that traverses the bypass line merges again into in the sampling line upstream of the sensors 12 and 14.

When the aforesaid instantaneous breath-by-breath measuring mode is selected, the pump 11 is kept permanently connected to the sampling line 8. When, instead, the aforesaid measuring mode with mixing chamber is selected, the switching valve 20 is controlled in a PWM mode for simulating a capacity that varies in proportion to the flow exhaled Q.

Consequently, the device 100 is able to operate selectively in both measuring modes, i.e., with average measurement when the flow of air traverses the sampling line 8 and traverses the mixing chamber 18 or else with instantaneous breath-by-breath measurement when the flow of air traverses the bypass line 28 and reconverges in the sampling line 8 upstream of the sensor means for detecting oxygen 12 and the sensor means for detecting carbon dioxide 14.

According to a further characteristic, in itself of a known type, the sampling line 8 includes a tube having a wall permeable to humidity, for example made of NAFION (registered trademark) to keep the humidity within the sampling line 8 substantially equal to ambient humidity.

The aforesaid tube with permeable wall enables removal of the humidity contained in the sample of exhaled air to be analysed.

The exhaled air is saturated with humidity, and the aforesaid tube enables reduction of the concentration of water vapour to obtain in the sample of air to be analysed the same humidity present in the environment.

According to a further innovative characteristic of the present invention, the device 100 comprises first humidity-sensing means 32 designed to detect the humidity of the flow of air within the sampling line 8, and second humidity-sensing means 34 designed to detect the humidity of the ambient air. The humidity-sensing means may be provided in any way in itself known.

The electronic control unit 6 is prearranged for receiving signals 32a and 34a emitted by the aforesaid first humidity-sensing means 32 and second humidity-sensing means 34, for comparing the values of humidity measured, and for activating an alarm signal when the difference between the aforesaid values exceeds a pre-set threshold, indicating the need to replace the aforesaid tube with permeable wall defining the aforesaid sampling line 8.

In particular, the alarm signal is activated when the concentration of water vapour in the flow of air within the sampling line 8 is higher than the concentration of the water vapour present in the external environment for a predetermined value.

It should be noted that the latter characteristics (provision of the humidity-sensing means 32 and 34 and consequent control for signalling automatically the need to replace the tube with permeable wall) may also constitute, taken in themselves, a further aspect of the present invention.

According to a further characteristic of the preferred embodiment, the device 100 comprises a calibration valve 36, arranged in the sampling line 8 and switchable between a first condition, for connection of the downstream stretch of the sampling line 8 with the air collecting member 2 for sampling the flow of air, and a second condition, for connection of the downstream stretch of the sampling line 8 with a further line for sampling the ambient air 38.

A device for absorbing carbon dioxide 40 is interposed in the aforesaid further line for sampling the ambient air 38 in order to completely remove the content of carbon dioxide in the flow of air that traverses the further line for sampling the ambient air 38.

The calibration valve 36 is switched into the second condition of connection of the sampling line 8 to the line for sampling the ambient air 38 when the device 100 is subjected to zero-setting of the sensor means for detecting carbon dioxide 14.

The electronic control unit 6 is provided for controlling the calibration valve 36 (line 36a) with actuator means of any known type for activating the aforesaid calibration mode.

Thanks to the aforesaid arrangement, the calibration operations consequently do not require the use of cylinders containing mixtures of gases without carbon dioxide.

As is evident from the foregoing description, the device according to the invention is simple and at the same time extremely functional.

It is able to operate both with average measurement by means of the mixing chamber and with instantaneous breath-by-breath measurement and can consequently be used for different applications, such as for example in the clinical field on patients or else in the context of sports medicine.

Thanks also to the small overall dimensions, the device can be used by athletes who wish to assess the aerobic power during dynamic physical exercise.

The device presents a high degree of efficiency thanks to the possibility of monitoring constantly the values of humidity and of enabling, at the appropriate moment, replacement of the tube with permeable wall that constitutes the sampling line.

A further advantage of the device forming the subject of the present invention is the extreme simplicity and accuracy of calibration thereof, which, thanks to the presence of a specific line for sampling the ambient air and of a device for absorbing carbon dioxide interposed in the aforesaid line, does not require the use of dedicated gas cylinders.

Of course, without prejudice to the principle of the invention, the structural details and the embodiments may vary widely with respect to what has been described and illustrated herein merely by way of example, without thereby departing from the scope of the present invention, as specified in the ensuing claims.

What is claimed is:

1. A device for measuring the consumption of oxygen and the elimination of carbon dioxide by a subject, comprising:
    an air collecting member for collecting a flow of air, which can be worn by the subject and has passages for air inhaled and exhaled by the subject;
    a flowmeter that can be associated to the collecting member for emitting signals indicative of the flow rate of air exhaled by the subject;
    a sampling line connected to the collecting member or to the flowmeter, for sampling a portion of the flow of air exhaled by the subject;
    a suction pump, with substantially constant capacity, arranged downstream of the sampling line, for drawing the aforesaid portion of flow of air into the sampling line;
    a mixing chamber interposed in the sampling line, upstream of the suction pump, for collecting and mixing together flows of air exhaled by the subject in a number of breathing cycles;
    means for sensing the concentration of oxygen, and means for sensing the concentration of carbon dioxide, arranged in the sampling line between the mixing chamber and the suction pump, for measuring the concentration of oxygen and of carbon dioxide in the flow of air that traverses the sampling line downstream of the mixing chamber;
    a switching valve for switching the intake of the pump between a condition of connection to the sampling line and a condition in which said connection is interrupted and the intake of the pump communicates with a line for intake of air from the environment;
    an electronic control unit for receiving and processing the signals emitted by said flowmeter, by said means for sensing the concentration of oxygen, and by said means for sensing the concentration of carbon dioxide in order to obtain an average measurement of the consumption of oxygen by the subject in the course of a number of breathing cycles;
    said electronic control unit being moreover provided for controlling said switching valve in a PWM mode in order to simulate a capacity of the suction pump that varies in proportion to the variation of the flow during the breathing cycle so as to render measurement of the consumption of oxygen reliable, even though the mixing chamber does not receive the entire flow exhaled by the subject,
    wherein said device further comprises:
    a bypass line parallel to the mixing chamber, through which the flow of air can pass without passing through the mixing chamber, said bypass line merging again into the sampling line upstream of the aforesaid sensor means;
    a valve for selecting a measuring mode, which can be displaced selectively into two different positions, to cause the flow of air that traverses the sampling line to converge either through the mixing chamber, when an average measurement is to be made of the consumption of oxygen by the subject in the course of a number of breathing cycles, or through said bypass line, when an instantaneous measurement is to be made of the consumption of oxygen by the subject in each breathing cycle,
    wherein said electronic control unit is configured to control said switching valve so that said pump is kept constantly connected to the sampling line when the aforesaid instantaneous measuring mode is selected, and
    wherein said sampling line includes a tube having a wall permeable to humidity to keep the humidity within the sampling line substantially equal to ambient humidity, said device further comprising:
    first humidity-sensing means for sensing the humidity of the flow of air within the sampling line; and
    second humidity-sensing means, adapted to detect the humidity of the ambient air,
    said electronic control unit being provided for comparing the values of humidity measured by said first and second humidity-sensing means and for activating an alarm signal when the difference between said values exceeds a pre-set threshold indicating the need to replace said tube with permeable wall defining said sampling line.

2. The device according to claim 1, wherein:
    the device further comprises a calibration valve, arranged in the sampling line and switchable between:
    a first condition, of connection of a downstream stretch of the sampling line with said collecting member for collecting a flow of air; and
    a second condition of connection of the downstream stretch of the sampling line to a further line for sampling the ambient air,
    said device further comprises a device for absorbing carbon dioxide interposed in said further line for sampling the ambient air to completely remove the content of carbon dioxide in the flow of air that traverses said further line for sampling the ambient air,
    said electronic control unit also being provided for controlling said calibration valve and activating a calibration mode, wherein said calibration valve is kept in said second condition, and said electronic control unit in said condition carries out calibration operations.

* * * * *